United States Patent [19]

Davidson

[11] Patent Number: Plant 7,728

[45] Date of Patent: Dec. 3, 1991

[54] ROSE PLANT: 'SMOOTH PERFUME'

[76] Inventor: Harvey D. Davidson, #3 El Verano Rd., Orinda, Calif., 94563

[21] Appl. No.: 638,439

[22] Filed: Jan. 3, 1991

[51] Int. Cl.[5] ..... A01H 5/00

[52] U.S. Cl. ..... Plt./11

[58] Field of Search ..... Plt. 11, 18, 19. 22, Plt./26, 27

*Primary Examiner*—Howard J. Locker

[57] ABSTRACT

A new rose variety of the hybrid tea class characterized by having large cream to light pink flowers with slightly lavender edges on a thornless bush with disease resistant glossy foliage.

1 Drawing Sheet

1

The present invention relates to a new and distinctive variety of rose plant of the hybrid tea class, which was originated by my crossing an unnamed cultivar resulting from a cross of 'Smooth Sailing' × 'Medallion' as the seed parent with 'Blue Moon' as the pollen parent.

Among the novel characteristics possessed by the new variety which distinguish it:

(a) From its parents and all other varieties of which I am aware are:
- (1) A plant which is thornless throughout.
- (2) A large cream to light pink flower with slightly lavender shadings on the outer petal edges.
- (3) Rapid flowering cycles.
- (4) Distinctive old rose damask fragrance.
- (5) A vigorous upright plant of medium height.

(b)

*Seed parent.*—A medium pink hybrid tea with thorns.

*Pollen parent.*—A lavender hybrid tea with thorns.

Asexual reproduction of the new rose variety by budding, as performed at Tulare, Calif. shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in the color description herein refers to plate numbers in the aforementioned color chart, e.g. "53A" is plate 53A" of The Royal Horticultural Society Colour Chart.

American Rose Society Registration commercial appellation: 'Smooth Perfume'

Parentage: Seedling.

*Seed parent.*—'Smooth Sailing' × 'Medallion'.

*Pollen parent.*—'Blue Moon'.

Class: Hybrid tea.

The following observations are made of specimens grown outdoors in Contra Costa County, Calif., in the month of September.

2

FLOWER

Blooming Habit

A. Bud:
- (1) *Size.*—Large.
- (2) *Form.*—Ovoid and pointed.
- (3) *Sepals.*—34 to 36 cm in length; to 10 mm extension beyond bud. No serration shown on sepal edges. Generally 1 out of 5 sepals show 2 appendages on each side of 1 to 3 mm length; heavy cotton matting on inner surface of sepals. Fine hairs on outer surface. Color before breaking — 144A; when turned down — 147C.
- (4) *Peduncle.*—Length — to 5.5 cm. Surface — smooth, no prickles or hairs. Strength — weak, slight curvature. Color — 144B flushed 172C.
- (5) *Color.*—When sepals first divide — outside petals 63C, shading to 65C.

B. Bloom:
- (1) *Size.*—Average when open — 12 cm.
- (2) *Borne.*—Singles and clusters of 2 to 4.
- (3) *Form.*—Cupped, semi-tight; rapid open; loose to maturity.
- (4) *Petalage.*—Average number — 28. Outer petals curled.
- (5) *Color.*—Early open — outside petals 63C to 65C, with veining 64D, aging to 63D. Inside petals 65C, aging to 56D.

C. Petals:
- (1) *Texture.*—Medium firm to tender.
- (2) *Appearance.*—Flexed; satiny; cream overcast pink-lavender pastel.
- (3) *Form.*—Evenly placed; slightly ruffled on edge.
- (4) *Arrangement.*—Regular at all stages; loose with aging.
- (5) *Petaloids in center.*—Average 3 to 4.
- (6) *Persistence.*—Drop off cleanly.
- (7) *Fragrance.*—Old rose damask.
- (8) *Lasting quality.*—Good on bush; moderate as cut flower.

REPRODUCTIVE ORGANS

A. Stamen:
- (1) *Arrangement.*—Regularly arranged around styles.
- (2) *Number.*—Average close to 160.
- (3) *Length.*—Average — 10 to 15 mm.
- (4) *Filaments.*—Color — base of anthers 62D, lower filament 62A.

(5) *Anthers.*—Color — 159A.

(6) *Pollen.*—15B.

B. Pistil:

(1) *Styles.*—3 to 6 mm lght., number close to 150; longitudinal striping 53A over white. Covered with fine white hairs at base.

(2) *Stigma.*—Color — Close to 53A.

(3) *Ovary.*—Rounded, 13 mm through center diameter.

C. Hips: Readily accepts own pollen, will accept some foreign pollen.

(1) *Shape.*—Rounded, flat base; to 2½ cm diameter, to 2 cm depth.

(2) *Color.*—When mature near 28B with shades of 42B.

(3) *Seed.*—Average number 4 to 6; not exposed.

PLANT

A. Form: Upright.

B. Growth: Vigorous; medium height — average 1.0 meter.

C. Foliage: Compound of 3 to 5 leaflets on bottom stem; 5 to 7 leaflets on main canes.

(1) *Size.*—Large.

(2) *Quantity.*—Stems well covered.

(3) *Color.*—New foliage upper side 178A, under side 146D with shades of 178A. Old foliage upper side near 148A, under side near 148B.

(4) *Shape.*—Oval with center pointed.

(5) *Texture.*—Upper side — leathery, glossy. Under side — smooth, dull.

(6) *Edge.*—Slight serration on outer edge. Average points 3 per 1 cm, with up to 1½ mm peak.

(7) *Rachis.*—Slight glandular hair on upper side; lower side occasional 4 to 5 hooked 1 mm prickles with about 1 to 1½ mm spacing.

(8) *Stipules.*—Average length 1.5 cm; auricle to 5 mm.

D. Resistance to disease: Mildew, rust and blackspot — very good.

E. Wood.

*New wood.*—Color near 146C, shadings of 178D; Bark — smooth.

*Old wood.*—Color near 146B, Bark — smooth.

F. Thorns: None.

G. Winter hardiness: Good.

I claim:

1. A new and distinct thornless variety of rose plant of the hybrid tea class, substantially as herein shown and described.

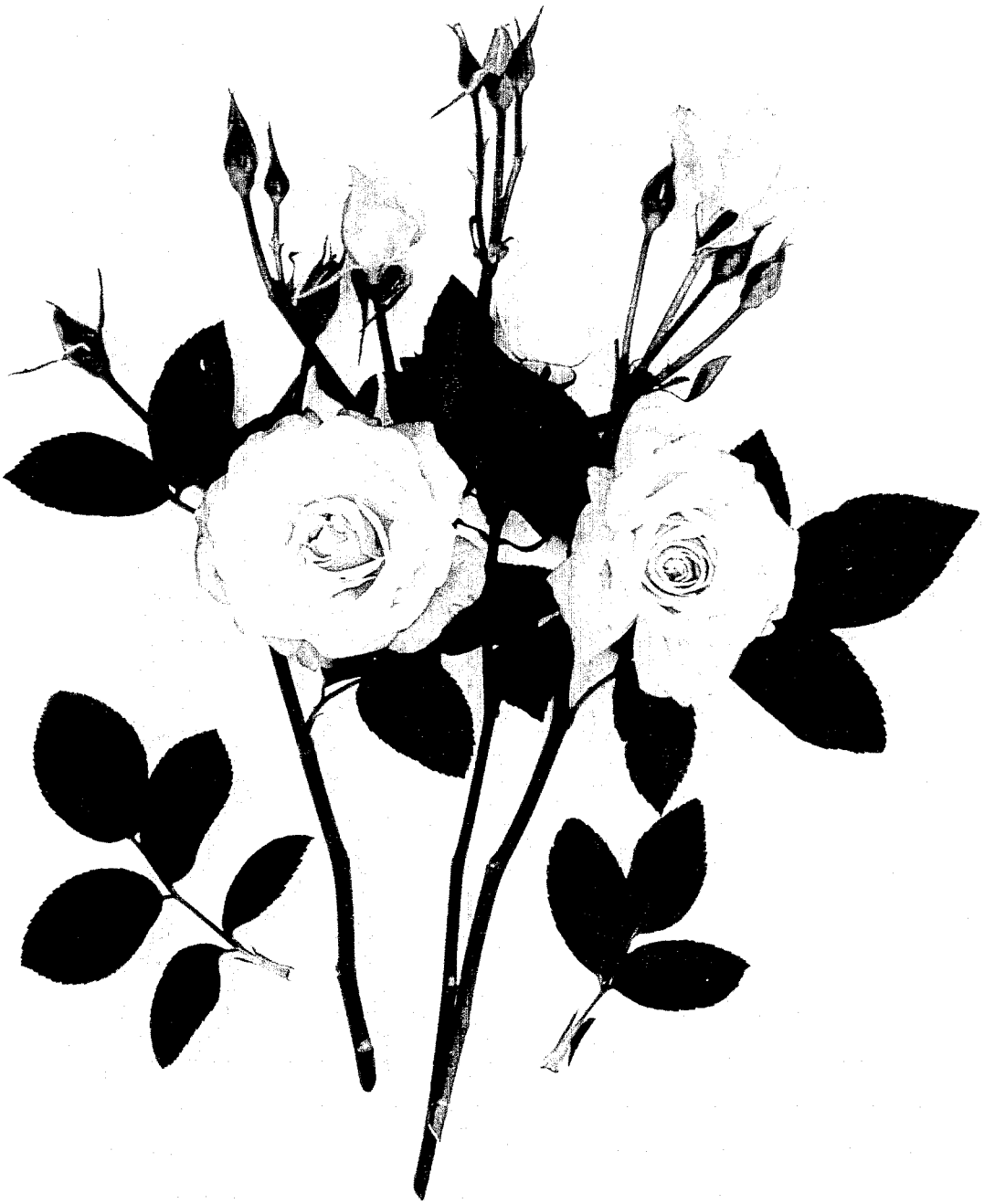

* * * * *